(12) United States Patent
Franklin et al.

(10) Patent No.: US 7,047,852 B2
(45) Date of Patent: May 23, 2006

(54) FEEDFORWARD CONTROL SYSTEM FOR AN ELASTIC MATERIAL

(75) Inventors: Kent Allan Franklin, Appleton, WI (US); Aaron Dee Schilpp, Appleton, WI (US); Douglas N. Duehring, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 443 days.

(21) Appl. No.: 10/001,207

(22) Filed: Oct. 24, 2001

(65) Prior Publication Data

US 2003/0075029 A1    Apr. 24, 2003

(51) Int. Cl.
B26D 7/14    (2006.01)

(52) U.S. Cl. .............................. 83/18; 83/42; 83/76.8; 83/289; 83/298; 83/367; 83/371; 83/937; 83/74; 83/312; 101/181; 604/358; 604/393

(58) Field of Classification Search ........... 198/810.01, 198/810.04; 226/29, 30; 242/534, 413.9, 242/413, 487.2, 523.1, 526, 527.5, 554.2; 73/159; 702/150, 151, 152; 700/175, 51, 700/167; 713/193; 156/510, 269, 64, 229, 156/250, 350, 378, 495; 604/385.04, 358, 604/393; 53/51, 229, 324, 361, 495; 83/298, 83/18, 22, 42, 75.5, 768, 289, 365, 367, 369, 83/371, 937, 938, 949, 76.4, 312, 74; 101/181, 101/248

See application file for complete search history.

(56) References Cited

U.S. PATENT DOCUMENTS

| | | | |
|---|---|---|---|
| 3,774,016 A | 11/1973 | Sterns et al. ............. 235/151.1 |
| 3,841,216 A | 10/1974 | Huffman ..................... 101/181 |
| 4,287,797 A | 9/1981 | Seragnoli ........................ 83/74 |
| 4,525,229 A | 6/1985 | Suzuki et al. ................ 156/161 |
| 4,543,863 A * | 10/1985 | Rader ............................. 83/76 |
| 4,635,511 A * | 1/1987 | Shirasu ........................... 83/74 |
| 4,719,575 A | 1/1988 | Gnuechtel .................... 364/469 |
| 4,726,874 A | 2/1988 | VanVliet ...................... 156/495 |
| 4,781,090 A | 11/1988 | Feldkamper et al. ........... 83/74 |
| 4,848,630 A | 7/1989 | Niestrath et al. ............... 226/4 |
| 4,947,685 A | 8/1990 | Montgomery et al. ........ 73/159 |
| 4,955,265 A | 9/1990 | Nakagawa et al. ............. 83/74 |
| 4,961,149 A | 10/1990 | Schneider et al. ........... 364/469 |
| 4,984,458 A | 1/1991 | Montgomery et al. ........ 73/159 |
| 5,000,806 A | 3/1991 | Merkatoris et al. .......... 156/161 |
| 5,045,135 A | 9/1991 | Meissner et al. .............. 156/64 |
| 5,091,039 A | 2/1992 | Ujimoto et al. ............. 156/519 |
| 5,095,219 A | 3/1992 | Laumann et al. ............ 250/548 |
| 5,104,116 A | 4/1992 | Pohjola ........................ 271/185 |
| 5,224,405 A | 7/1993 | Pohjola .......................... 83/24 |
| 5,235,515 A | 8/1993 | Ungpiyakul et al. ......... 364/469 |
| 5,241,884 A * | 9/1993 | Smithe et al. ................... 83/76 |

(Continued)

FOREIGN PATENT DOCUMENTS

JP    06-297385    10/1994

(Continued)

*Primary Examiner*—Boyer D. Ashley
(74) *Attorney, Agent, or Firm*—Pauley Petersen & Erickson

(57) ABSTRACT

A process for providing feedforward control to control the feed rate of an elastic material. The process involves measuring the distance between registration marks on the elastic material prior to cut-off. These measurements are compared to a target cut length. The feed rate of a feed roll is adjusted, based on the target cut length and the distance between the registration marks, to maintain the cut length of the elastic material at the target cut length.

55 Claims, 4 Drawing Sheets

U.S. PATENT DOCUMENTS

| | | | |
|---|---|---|---|
| 5,286,317 A | 2/1994 | Treat et al. | 156/64 |
| 5,295,571 A * | 3/1994 | Van Den Bogaert et al. | 198/502.1 |
| 5,296,080 A | 3/1994 | Merkatoris et al. | 156/496 |
| 5,359,525 A | 10/1994 | Weyenberg | 364/469 |
| 5,361,960 A * | 11/1994 | Fokos et al. | 226/2 |
| 5,429,694 A | 7/1995 | Herrmann | 156/164 |
| 5,480,085 A * | 1/1996 | Smithe et al. | 226/44 |
| 5,500,063 A | 3/1996 | Jessup | 156/85 |
| 5,540,796 A | 7/1996 | Fries | 156/164 |
| 5,556,504 A | 9/1996 | Rajala et al. | 156/519 |
| 5,659,538 A | 8/1997 | Stuebe et al. | 236/469.02 |
| 5,669,996 A | 9/1997 | Jessup | 156/85 |
| 5,716,478 A | 2/1998 | Boothe et al. | 156/302 |
| 5,759,340 A | 6/1998 | Boothe et al. | 156/519 |
| 5,858,143 A | 1/1999 | Bright et al. | 156/86 |
| 5,899,128 A | 5/1999 | Smithe et al. | |
| 5,915,612 A | 6/1999 | Hinton | 226/30 |
| 5,964,970 A | 10/1999 | Woolwine et al. | |
| 6,033,502 A * | 3/2000 | Coenen et al. | 156/64 |
| 6,112,658 A | 9/2000 | Gunther et al. | 101/171 |
| 6,209,817 B1 | 4/2001 | Conrad et al. | |
| 6,371,902 B1 * | 4/2002 | Bluemle | 493/422 |

FOREIGN PATENT DOCUMENTS

| | | |
|---|---|---|
| WO | 01/01211 | 1/2001 |
| WO | WO 01/68319 A1 | 9/2001 |

* cited by examiner

FEEDFORWARD CONTROL SYSTEM FOR AN ELASTIC MATERIAL

BACKGROUND OF THE INVENTION

This invention is directed to a process for providing feedforward control for controlling an amount of elastic material that is fed as part of a larger material handling or converting process.

A number of different manufacturing processes are used to cut continuous webs of elastic material, such as stretch-bonded laminates, into discrete lengths prior to placement in an absorbent garment or other application. Such processes often include feedback control to correct the cut length of the material when cut length errors are detected. The "cut length" is the length of stretch-bonded laminate (SBL), or other elastic material, between consecutive cuts in the machine direction. Feedback control for the cut length of an elastic material typically relies on a cut length error to determine the magnitude of a process correction, with the cut length error being the difference between a measured cut length and a target cut length.

Research has shown that there can be a "stretchability" gradient from the beginning to the end of an SBL roll. For example, if a piece of SBL is cut at the beginning of a roll under a certain tension, and a piece is cut at the end of a roll under that same tension, the cut at the end of the roll may be longer. In a feedback control system, this change in cut length caused by a change in material properties cannot be corrected until an error in cut length has been detected after the panels have been cut. Consequently, sudden changes in material properties or process conditions can result in large errors in cut length because the system is not aware of a change in cut length until after the elastic material is cut.

SUMMARY OF THE INVENTION

In response to the discussed difficulties and problems encountered in the prior art, a new method of controlling the feed rate of an elastic material has been discovered.

The present invention is directed to a process using a feedforward or predictive control system to reduce the impact of changes in material properties or process variations, such as material splices, on elastic cut length. In general, the process provides a way to control the length of web material being fed, and to modify it rapidly when needed, based on information received from the process. As mentioned, the process is used to control feed rate, but it can also be used to control cut length and other properties, such as web tension.

Material properties may not be controllable within or between rolls or boxes; however, the present invention provides control over the rate at which a web is fed within a converting process. The feed rate is controlled to correspond to a target feed rate that relates to the length of a material under zero tension. As the material properties change, the target feed rate may also change.

More specifically, the process involves measuring the distance between registration marks on the elastic material prior to the cut-off. These measurements are used as an input to the control system to control cut length directly, or in conjunction with measured cut length, to determine the feed roll speed correction needed to maintain the elastic cut length at a target cut length.

The invention may also be used to register the cutting of an elastic material containing a registered graphic such that each piece of elastic material contains the graphic.

With the foregoing in mind, it is a feature and advantage of the invention to provide a process for providing feedforward control to control cut length of an elastic material.

It is another feature and advantage of the invention to provide a process for providing a way to control web feed rate, or the amount of material being fed within a process, and to modify it rapidly when needed, based on information received from the process.

DEFINITIONS

"Absorbent garment" refers to training pants, diapers, incontinence products, other personal care or health care garments, including medical garments, or the like.

"Elastic" and "Elasticity" refer to the tendency of a material, or composite material, to recover its original size and shape after removal of the force causing a deformation.

"Machine direction" refers to the length of a fabric in the direction in which it is produced, as opposed to "cross direction" which refers to the width of a fabric in a direction generally perpendicular to the machine direction.

"Stretch-bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Tension" refers to a force tending to cause the extension of a body, or the balancing force within that body resisting the extension.

DETAILED DESCRIPTION OF THE PRESENTLY PREFERRED EMBODIMENTS

The present invention is directed to a process for providing feedforward control to control the amount of an elastic material that is fed as part of a larger material handling or converting process. Feedforward or predictive control reduces the impact of changes in material properties or process upsets on the amount of elastic material that is fed during a process step. The feedforward control is accomplished by measuring a distance between registration marks on the elastic material. These measurements are used as an input to a control system to directly control the amount of material that is fed, or to control the amount that is fed in conjunction with measured amounts of material that have been fed, to determine a feed roll speed correction needed to maintain the amount of elastic material that will be fed at a target level. For ease of explanation, the description hereafter will be in terms of a process to control cut length of an elastic material.

Figure 1:
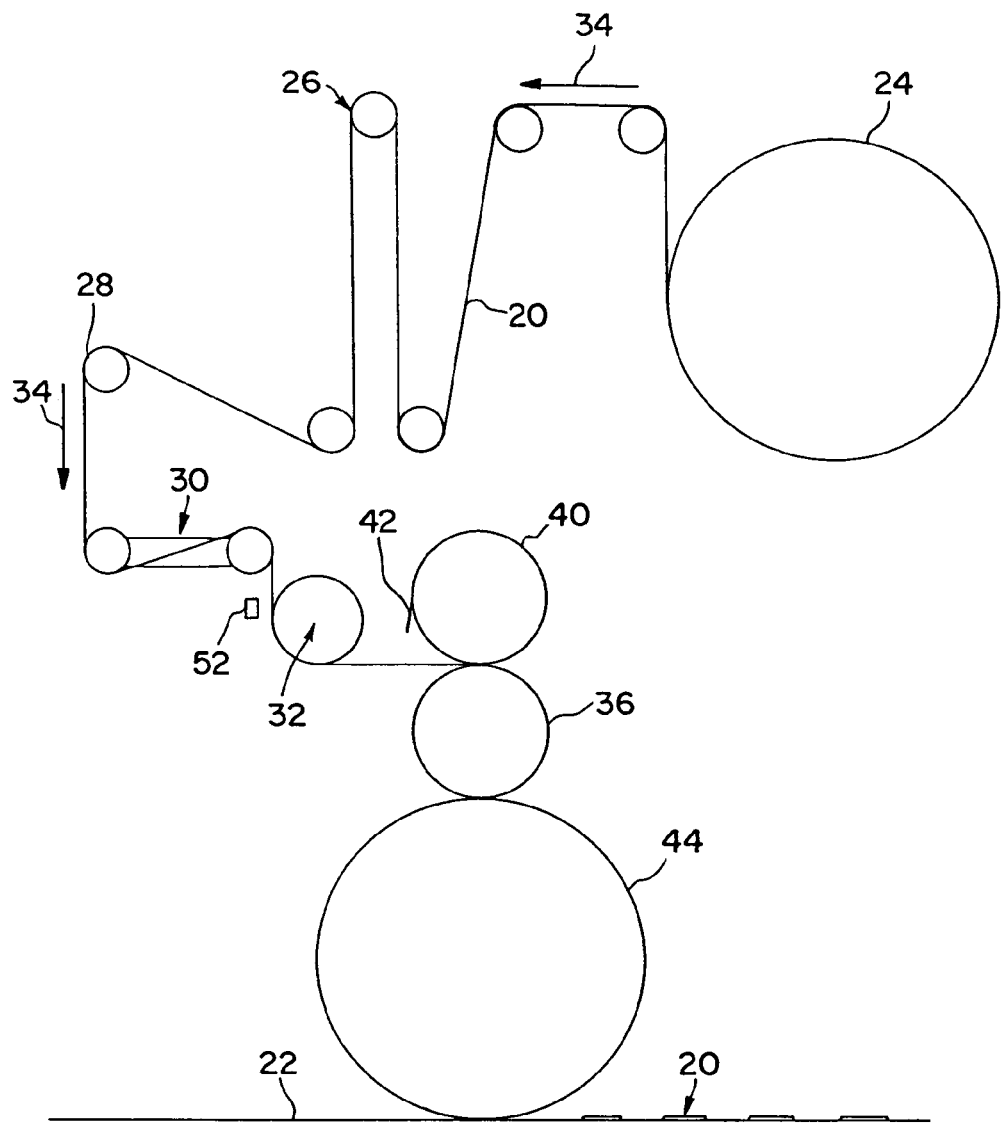
FIG. 1 illustrates a process diagram for cutting and placing pieces of elastic material onto a moving web.

FIG. 1 is a diagram of one example of a process that can be used to cut-and-place pieces of elastic material 20, such as stretch-bonded laminate (SBL), onto a moving web 22. In this case, the pieces of elastic material 20 can be used to form side panels of an absorbent garment.

First, elastic material 20 is unwound from an unwind device 24, such as an unwind device available from Martin Automatic, Inc., Rockford, Ill. Alternatively, two or more unwind devices 24 can be used, for example, with one unwind device 24 supplying a first side and another unwind device 24 supplying a second side. The elastic web 20 can pass over a dancer roll 26, as shown in FIG. 1, which can serve as a means to control tension in the web 20. Alternatively, the web tension could be controlled by running the web 20 around a driven roll (in place of the dancer roll 26 shown in FIG. 1) which is followed by a roller bar 28 that measures the web tension. The web 20 can then pass through a web guide 30. A web guide 30 can be used to control the positioning of the web 20 along a cross-direction of the process in preparation for being fed onto a vacuum feed roll 32. For the purposes of the present invention, the cross-direction lies generally within the plane of the material being transported through the process and is aligned perpendicular to the machine direction. The machine direction is indicated by arrows 34 in FIG. 1.

The vacuum feed roll 32 controls the rate at which the elastic material 20 is fed to an anvil roll 36, and, along with web tension and material properties, determines the cut length. The elastic material 20 is cut into pieces of discrete length when positioned between the anvil roll 36 and a nip roll 40, with the nip roll 40 including a cutting mechanism 42 such as one or more blades. The anvil roll 36 is suitably covered with vacuum holes that hold the pieces of elastic material 20 until the pieces of elastic material 20 are released to a side panel applicator 44 or other application device. An example of a suitable side panel applicator 44 is described in detail in U.S. Pat. No. 5,224,405 which is hereby incorporated by reference. The side panel applicator 44 places the pieces of elastic material 20 on a product to form, for example, side panels on an absorbent garment.

Figure 3:
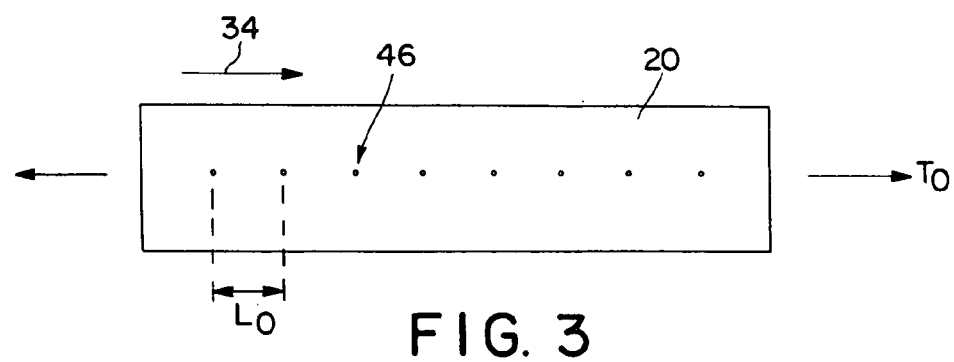
FIG. 3 illustrates a top view of a piece of elastic material under zero tension, $T_0$.

To provide feedforward control in the system, regularly spaced registration marks 46 are placed on the elastic web 20, as shown in FIG. 3, and the distance between the registration marks 46 is measured just prior to feeding the elastic material 20 onto the vacuum feed roll 32. These measurements provide a predictive input to the control system 48 (FIG. 6), which in turn adjusts the speed of the feed roll 32 which adjusts the feed rate of the elastic material 20, to reduce the impact of unexpected changes in material properties. Alternatively, instead of adjusting the speed of the feed roll 32, the control system 48 may adjust tension in the elastic web 20 to change the amount of material cut off.

Research has shown that there is an equation that governs elastic material properties and how these properties relate to process cut length. The equation is relative to a Tension vs. Strain curve 50 of an exemplary elastic material 20, shown in FIG. 2. The equation is:

$$L_c = (E)(L_s)/(E+T-A) \quad (1)$$

wherein, $L_c$ is the cut length, or the amount of elastic material in the machine direction that is cut and measured in units of centimeters/product, for example;

E is the Initial Modulus, or slope of the line through 10–30% strain on the Tension vs. Elastic Material Strain curve (FIG. 2), which may be measured in units of grams/centimeter, for example;

$L_s$ is the feed rate of the elastic material, or speed of the vacuum feed roll, which may be measured in units of centimeters/product, for example;

T is the amount of tension applied to the elastic web, which may be measured in units of grams/centimeter, for example; and A is the Initial Intercept, or y-intercept of the Initial Modulus (E) line, which may be measured in units of grams/centimeter, for example.

One way to estimate the modulus and intercept in process is to apply the following equation:

$$\text{Strain} = \Delta L/L \quad (2)$$

where L is length of the elastic material 20 under zero tension and $\Delta L$ is the change in length that results when the material is placed under a tension T. Strain is inversely proportional to length, according to Equation (2). As a result, it is possible to take an on-line length measurement and relate it to tension in order to estimate a portion of the graph in FIG. 2.

An on-line length measurement can be obtained by measuring the distance between the registration marks 46 on the elastic material 20. The registration marks 46 can be any type of suitable mark, such as a line, a spot, a hole, an optical brightener, or a material detectable in near-IR or generally outside the visible light range. The registration marks 46 can be applied to the elastic material 20 during the manufacturing process, the manufacturing process being the process that makes the elastic material. Alternatively, the registration marks 46 can be applied to the elastic material 20 during the converting process, suitably at a location under low web tension. A sensor 52, such as a photoeye available from Banner Engineering Corp. of Minneapolis, Minn., can be used to detect the registration marks 46 during the converting process, the converting process being the process that takes place from material leaving its as-manufactured state, such as from a roll or festoon, to incorporation of the material into an article of manufacture. For example, the converting process may take place from the vacuum feed roll 32 to the side panel applicator 44.

When the elastic material 20 is in a relaxed state, tension, $T_0$, in the elastic web 20 is negligible. Tension, $T_1$, in the elastic web 20 during the manufacturing process is the amount of tension in the elastic web 20 during application of the registration marks 46. Tension, $T_2$, in the elastic web 20 during the converting process is the amount of tension in the elastic web 20 while being fed onto the vacuum feed roll 32.

Figure 4:
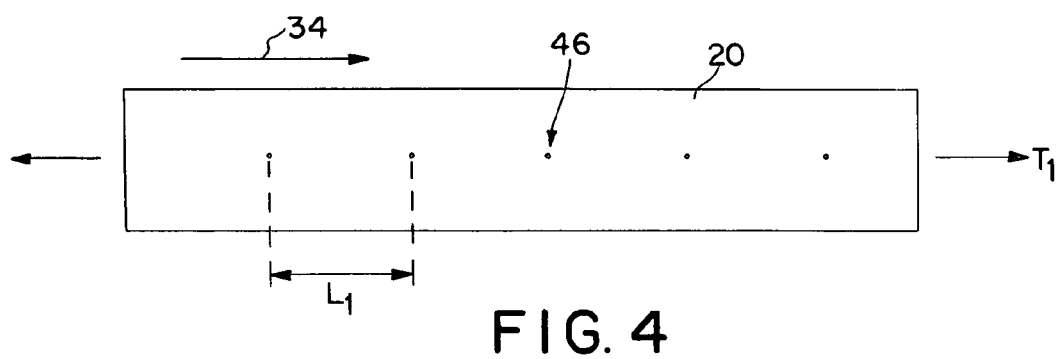
FIG. 4 illustrates a top view of a piece of elastic material under manufacturing tension, $T_1$.
Figure 5:
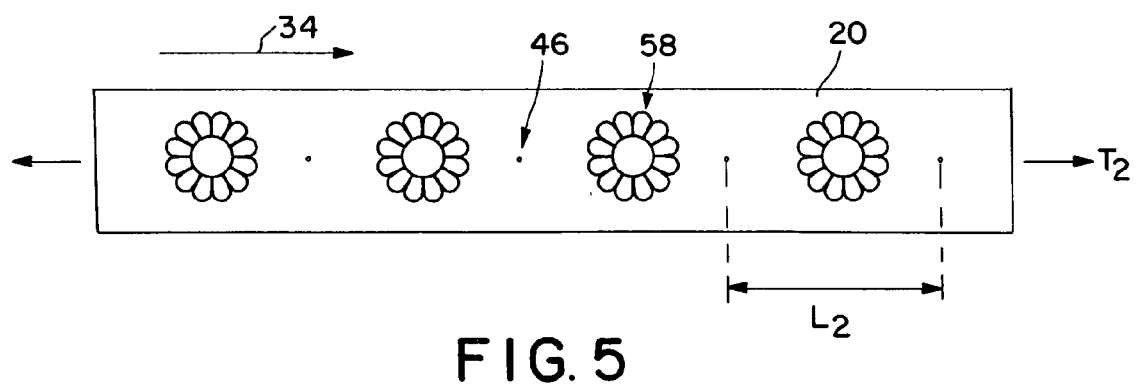
FIG. 5 illustrates a top view of a piece of elastic material under converting tension, $T_2$.

A distance, $L_0$, between the registration marks 46 while the elastic web 20 is under zero tension, $T_0$, is illustrated in FIG. 3. A distance, $L_1$, between the registration marks 46 while the elastic web 20 is under the manufacturing tension, $T_1$, is illustrated in FIG. 4. A distance, $L_2$, between the registration marks 46 while the elastic web 20 is under the converting tension, $T_2$, is illustrated in FIG. 5. The distance, $L_2$, between the registration marks 46 can be measured either just prior to feeding the elastic material 20 onto the vacuum feed roll 32, or while the elastic material 20 is on the vacuum feed roll 32.

Using the points $(S_1, T_1)$ and $(S_2, T_2)$, the Tension vs. Elastic Material Strain relationship can be approximated by a straight line. As a result, the Initial Modulus and Initial Intercept can be estimated with the two points $(S_1, T_1)$ and ($S_2$, $T_2$), shown in FIG. 2. For the following equations, tension is measured as a force per unit width.

$$S_1=(L_1-L_0)/L_0 \qquad (3)$$

$$S_2=(L_2-L_0)/L_0 \qquad (4)$$

Since E is the slope of the line, it follows that:

$$E=(T_2-T_1)/(S_2-S_1) \qquad (5)$$

Substituting Equations 3 and 4 into Equation 5, results in:

$$E=(T_2-T_1)L_0/(L_2-L_1) \qquad (6)$$

The well-known straight line equation is:

$$y=mx+b \qquad (7)$$

wherein m is the slope of the line ($\Delta y/\Delta x$), b is a constant, and x and y are distances along the respective axes. Substituting the point ($S_2$, $T_2$), the slope (E), and the Initial Intercept (A) into Equation 7, the following relationship is derived:

$$T_2=(E)(S_2)+A \qquad (8)$$

Substituting Equations 4 and 6 into Equation 8 results in the following:

$$A=T_2-[(T_2-T_1)(L_2-L_0)]/(L_2-L_1) \qquad (9)$$

Substituting Equations 6 and 9 into Equation 1 results in the following:

$$L_c=L_0L_s/L_2 \qquad (10)$$

From Equation 10, the feed rate, $L_s$, of the elastic material is:

$$L_s=L_cL_2/L_0 \qquad (11)$$

The distance, $L_0$, between the registration marks 46 when the elastic material 20 is under zero tension, $T_0$, may be determined in three different ways. First, the distance $L_0$ could be experimentally determined by taking offline measurements. Secondly, at small converting process tensions, the manufacturing process distance, $L_1$, maybe an acceptable estimate of $L_0$. Finally, the distance $L_0$ can be theoretically calculated and expressed in terms of known quantities.

Figure 2:
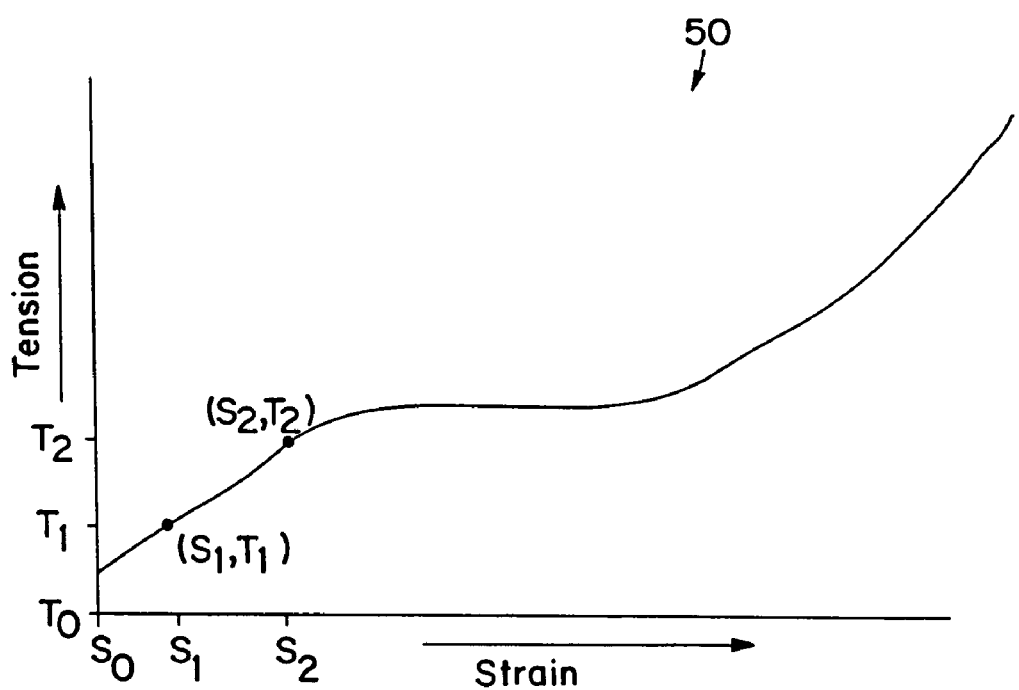
FIG. 2 illustrates a graph of Tension vs. Strain for a stretch-bonded laminate material.

The restatement of Equation 11 relies on the previously mentioned approximation of a straight line relationship between tension and elastic material strain (FIG. 2). Since T values are correlated with S values on the graph, the slope, m, of the line can be expressed as:

$$m=(T_2-T_1)/(S_2-S_1) \qquad (12)$$

Substituting Equations 3 and 4 into Equation 12 yields:

$$m=(T_2-T_1)/\{((L_2-L_0)/L_0)-((L_1-L_0)/L_0)\} \qquad (13)$$

Substituting Equation 13 and the point ($T_2$, $S_2$) into the standard equation of a line (y=mx+b) and canceling like terms produces Equation 14:

$$T_2=\{(T_2-T_1)(L_2-L_0)/(L_2-L_1)\}+b \qquad (14)$$

From Equation 14, the y-intercept, b, can be calculated as:

$$b=T_2-\{(T_2-T_1)(L_2-L_0)/(L_2-L_1)\} \qquad (15)$$

Plugging Equations 13 and 15 into the standard line equation results in the following line equation:

$$y=\{(T_2-T_1)/(L_2-L_1)\}x+\{T_2-((T_2-T_1)(L_2-L_0)/(L_2-L_1))\} \qquad (16)$$

When the tension, T, (the y value) is zero, the strain (x value) is also zero and the first term of the equation drops out. Thus, Equation 16 can be solved for $L_0$ in the following way:

$$L_0=L_2-\{T_2(L_2-L_1)/(T_2-T_1)\} \qquad (17)$$

Substituting Equation 17 into Equation 11 results in:

$$L_s=L_cL_2/\{L_2-(T_2(L_2-L_1)/(T_2-T_1))\} \qquad (18)$$

The cut length, $L_c$, used in Equations 11 and 18 is a target cut length, or target distance. Equations 11 and 18 can be used in a control system as the basis for scaling the feed rate, $L_s$, of the elastic material 20 (or speed of the vacuum feed roll (VFR) 32), either with or without cut length feedback. The feed rate, $L_s$, of the elastic material 20 (or speed of the VFR 32) is adjusted in order to achieve cut pieces of the elastic material 20 each having a length approximately equal to the target cut length, $L_c$. An adjustment factor, K, may be used in the adjustment function shown in Equation 18.

$$KL_2/L_1 \text{ or } KL_2/L_0, \text{ where } K>0 \qquad (19)$$

Alternatively, instead of comparing a measured length to a target length, the process of the invention can compare a measured feed rate to a target feed rate. As long as the ratio of $L_2/L_1$ or $L_2/L_0$, used as a comparator, remains fixed, the cut length will remain approximately constant.

Figure 6:
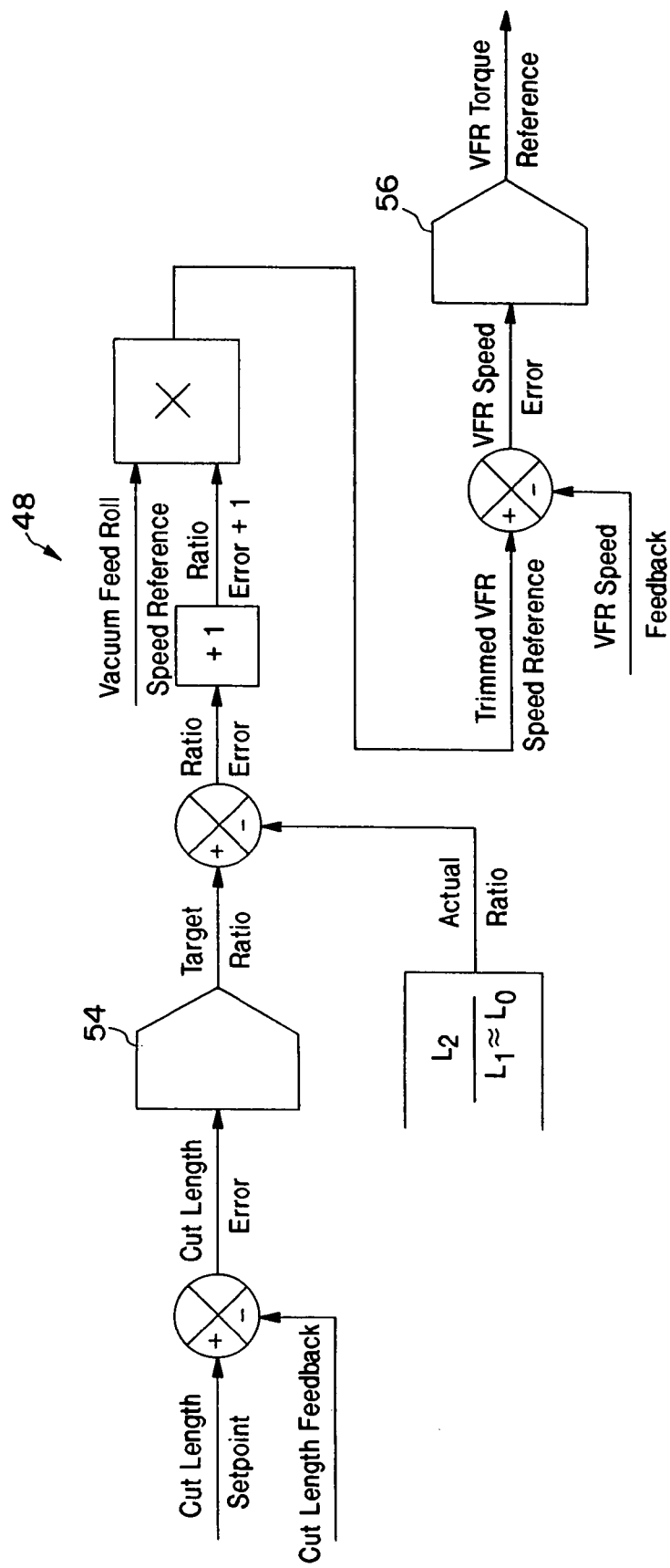
FIG. 6 illustrates schematically a feedforward cut length control system.

FIG. 6 is an example of a possible control system 48 that can be used in conjunction with the process shown in FIG. 1, for example. As shown in FIG. 6, the target cut length, or cut length setpoint, and the cut length feedback are input into the system 48. The cut length feedback, namely the actual measurements of pieces of elastic material 20 that have already been cut in the process, can be obtained from an automatic registration and inspection system. The detection of a cut length error can prompt a signal to a first control algorithm such as a proportional integral (PI) controller 54 which can be optimally tuned to achieve the target cut length. The first controller 54 can calculate a target ratio. An actual ratio of a measured distance, $L_2$, between the registration marks 46 while the elastic material 20 is under the converting tension, $T_2$, to a manufactured distance, $L_1$, between the registration marks can also be calculated. The target ratio and the actual ratio can then be compared. As explained above, at low tension, $L_1$ approaches, and can be used to approximate, $L_0$. Additionally, the exact relationship between $L_1$, and $L_0$, can be determined experimentally. The distance between registration marks can affect the response time. Shorter response times may result from shorter distances between marks.

A comparison of the target ratio to the actual ratio results in a ratio error. The system adds "1" to the ratio error and compares the result to the VFR speed reference, further resulting in a trimmed VFR speed reference. The trimmed VFR speed reference is compared to a VFR speed feedback. The detection of a VFR speed error prompts a signal to a second control algorithm, such as a second PI controller 56. The second PI controller 56 calculates a VFR torque reference, which then adjusts the speed of the VFR 32.

The control system 48 can also function without the cut length feedback and instead rely upon the target cut length and the measured ratio, $L_2/L_1$, between the registration marks 46 to adjust the speed of the VFR 32.

The process of the invention can also be used for cutting elastic material 20 containing a machine direction registered graphic 58, as shown in FIG. 5. More particularly, after initially increasing or decreasing the speed of the VFR 32 to center the graphic 58 relative to the cut edges, the feed rate of the elastic material 20 can be controlled so that the graphic 58 remains approximately centered between the cuts. The graphic 58 is thus registered in a machine direction relative to the registration marks 46, such that the graphic 58 may be either between consecutive registration marks 46 or aligned with the registration marks 46. Used in this manner, the process of the invention can provide each piece of cut elastic 20 with a centered graphic 58.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A process for providing feedforward control to control a feeding of an elastic material to a target feed rate, comprising the steps of:
   determining a machine direction distance, $L_1$, between a first registration mark and a second registration mark on an elastic material while the elastic material is under a first tension, $T_1$;
   approximating a machine direction distance, $L_0$, between the first registration mark and the second registration mark on the elastic material as if the elastic material were under zero tension, $T_0$;
   feeding the elastic material at a second tension, $T_2$;
   measuring a machine direction distance, $L_2$, between the first registration mark and the second registration mark on the elastic material while the elastic material is under the second tension, $T_2$; and
   adjusting a feed rate $L_s$, of the elastic material according to a given relation, to match a predetermined target feed rate.

2. The process of claim 1, further comprising the step of unwinding the elastic material from at least one unwind device under the first tension, $T_1$.

3. The process of claim 1, further comprising the step of approximating the machine direction distance, $L_0$, as a function of the first tension, $T_1$, and the machine direction distance, $L_1$.

4. The process of claim 1, further comprising the step of approximating the machine direction distance, $L_0$, as a function of the first tension, $T_1$, the machine direction distance, $L_1$, the second tension, $T_2$, and the machine direction distance, $L_2$.

5. The process of claim 1, wherein the elastic material comprises a graphic registered in a machine direction relative to the first registration mark and the second registration mark.

6. The process of claim 5, wherein the graphic comprises the first registration mark.

7. The process of claim 1, further comprising the step of applying the first registration mark and the second registration mark to the elastic material while the elastic material is under the first tension, $T_1$.

8. The process of claim 7, wherein the first and second registration marks are applied to the elastic material during a manufacturing process.

9. The process of claim 7, wherein the first and second registration marks are applied to the elastic material during a converting process.

10. The process of claim 9, wherein the converting process comprises the step of feeding the elastic material using a vacuum roll.

11. The process of claim 1, wherein the process is used to control a cut length of an elastic material to a target cut length, $L_c$, to form an elastic material segment.

12. The process of claim 11, further comprising the step of forming the elastic material segment into a side panel for an absorbent garment.

13. An absorbent garment comprising the side panel formed by the process of claim 12.

14. The process of claim 11, further comprising the step of adjusting the feed rate, $L_s$ of the elastic material using an adjustment factor, $K$, as $KL_2/L_0$, wherein $K>0$.

15. The process of claim 10, wherein the feed rate, $L_s$, of the elastic material is adjusted according to the relation:

$$L_s = L_c L_2 / L_0.$$

16. A process for providing feedforward control to control cut length of an elastic material to a target cut length, $L_c$, comprising the steps of:
    using a feed roll to feel an elastic material at a converting tension, $T_2$;
    measuring a machine direction distance, $L_2$, between a first registration mark and a second registration mark on the elastic material while the elastic material is under the converting tension, $T_2$;
    adjusting a feed rate of the elastic material according to a given relation utilizing the machine direction distance, $L_2$, to match a predetermined target cut length, $L_c$;
    adjusting a speed of the feed roll to control the target cut length, $L_c$ according to the relation:

$$\text{SPEED}_{feed\ roll} = L_c L_2 / L_0;$$

wherein $L_0$ is an approximated machine direction distance between the first registration mark and the second registration mark on the elastic material as if the elastic material were under zero tension; and
    cutting a length of the elastic material approximately equal to the target cut length, $L_c$, to form an elastic material segment.

17. The process of claim 16, further comprising the step of adjusting the speed of the feed roll using an adjustment factor, $K$, as $KL_2/L_0$, wherein $K>0$.

18. The process of claim 16, wherein the feed rate is further adjusted in response to cut length feedback.

19. The process of claim 16, wherein the first and second registration marks are applied to the elastic material during a manufacturing process.

20. The process of claim 16, wherein the first and second registration marks are applied to the elastic material during a converting process.

21. The process of claim 16, wherein the machine direction distance, $L_2$, is measured prior to the elastic material reaching the feed roll.

22. The process of claim 16, wherein the machine direction distance, $L_2$, is measured while the elastic material is on the feed roll.

23. The process of claim 16, wherein the elastic material comprises a graphic registered in a machine direction relative to the first registration mark and the second registration mark.

24. The process of claim 23, wherein the graphic comprises the first registration mark.

25. The process of claim 16, further comprising the step of forming the elastic material segment into a side panel for an absorbent garment.

26. An absorbent garment comprising the side panel formed by the process of claim 25.

27. The process of claim 1, further comprising the steps of unwinding the elastic material from at least one unwind device under a first tension, $T_1$; applying the first registration mark and the second registration mark to the elastic material while the elastic material is under the first tension, $T_1$; and measuring a machine direction distance, $L_1$, between the first registration mark and the second registration mark while the elastic material is under the first tension, $T_1$.

28. The process of claim 27, comprising the step of approximating a machine direction distance, $L_0$, between the first registration mark and the second registration mark on the elastic material as if the elastic material were under zero tension, $T_0$, as a function of the first tension, $T_1$, and the machine direction distance, $L_1$.

29. The process of claim 27, comprising the step of approximating a machine direction distance, $L_0$, between the first registration mark and the second registration mark on the elastic material as if the elastic material were under zero tension, $T_0$, as a function of the first tension, $T_1$, the machine direction distance, $L_1$, the converting tension, $T_2$, and the machine direction distance, $L_2$.

30. A process for providing feedforward control to control cut length of an elastic material to a target cut length, comprising the steps of:
   transferring the elastic material to a feed roll;
   approximating a distance between a first registration mark and a second registration mark on the elastic material as if the elastic material were under zero tension;
   determining a distance between the first registration mark and the second registration mark on the elastic material while the elastic material is under tension;
   comparing a target ratio of the distance under tension to the distance under approximately zero tension to an actual ratio of the distance under tension to the distance under approximately zero tension;
   adjusting a speed of the feed roll in response to any difference between the target ratio and the actual ratio of the distance under tension to the distance under approximately zero tension; and
   cutting a length of the elastic material approximately equal to the target cut length, to form an elastic material segment.

31. The process of claim 30, wherein the distance between the first registration mark and the second registration mark while the elastic material is under tension is measured while the elastic material is on the feed roll.

32. The process of claim 30, wherein the first and second registration marks are applied to the elastic material during a manufacturing process.

33. The process of claim 30, wherein the first and second registration marks are applied to the elastic material during a converting process.

34. The process of claim 30, further comprising the step of applying the first registration mark and the second registration mark to the elastic material while the elastic material is under tension.

35. The process of claim 30, wherein the speed of the feed roll is adjusted as a function of the target distance, the distance between the first registration mark and the second registration mark while the elastic material is under tension, and the approximated distance between the first registration mark and the second registration mark as if the elastic material were under zero tension.

36. The process of claim 35, wherein the speed of the feed roll is further adjusted in response to cut length feedback.

37. The process of claim 30, wherein the elastic material comprises a graphic registered in a machine direction relative to the first registration mark and the second registration mark.

38. The process of claim 37, wherein the graphic comprises the first registration mark.

39. The process of claim 30, further comprising the step of adjusting the speed, $L_s$, of the feed roll using an adjustment factor, K, as $KL_2/L_0$, wherein K>0, $L_2$ is the distance between the first registration mark and the second registration mark while the elastic material is under tension, and $L_0$ is the approximated distance between the first registration mark and the second registration mark as if the elastic material were under zero tension.

40. The process of claim 39, wherein the speed, $L_s$, of the feed roll is adjusted according to the relation:

$$L_s=L_c/L_2,$$

wherein $L_c$ is the target cut length.

41. The process of claim 30, further comprising the step of forming the elastic material segment into a side panel for an absorbent garment.

42. An absorbent garment comprising the side panel formed by the process of claim 41.

43. A process for providing feedforward control to control a speed at which an elastic material is fed into a convening process, comprising the steps of:
   feeding the elastic material into a converting process at a first feed rate;
   determining a first distance between a first registration mark and a second registration mark on the elastic material while the elastic material is under a first tension;
   determining a second distance between the first registration mark and the second registration mark on the elastic material while the elastic material is under a second tension;
   determining a target feed rate for the elastic material based on a relationship between the first and second distances; and
   adjusting the first feed rate of the elastic material in response to any difference between the target feed rate and the first feed rate to make the first feed rate match the target feed rate.

44. The process of claim 43, further comprising the step of applying the first registration mark and the second registration mark to the elastic material while the elastic material is under the first tension.

45. The process of claim 43, wherein the distance between the first registration mark and the second registration mark while the elastic material is under the first tension is measured while the elastic material is on the feed roll.

46. The process of claim 43, wherein the first and second registration marks are applied to the elastic material during a manufacturing process.

47. The process of claim 43, wherein the first and second registration marks are applied to the elastic material during the converting process.

48. The process of claim 43, further comprising the step of adjusting the first feed rate, $L_s$, of the elastic material using an adjustment factor, K, as $KL_2/L_0$, wherein K>0, $L_2$ is the first distance between the first registration mark and the second registration mark while the elastic material is under the first tension, and $L_0$ is the second distance between the first registration mark and the second registration mark while the elastic material is under the second tension.

49. The process of claim 48, wherein the first feed rate, $L_s$, of the elastic material is adjusted according to the relation:

$$L_2 = L_c L_2 L_0,$$

wherein $L_c$ is a target cut length.

50. The process of claim 43, further comprising the step of forming the elastic material segment into a side panel for an absorbent garment.

51. An absorbent garment comprising the side panel formed by the process of claim 50.

52. The process of claim 43, further comprising the step of approximating a distance between the first registration mark and the second registration mark as if the elastic material were under zero tension.

53. The process of claim 52, wherein the feed rate of the elastic material is adjusted as a function of the target feed rate, the second distance between the first registration mark and the second registration mark while the elastic material is under the second tension, and the distance between the first registration mark and the second registration mark as if the elastic material were under zero tension.

54. The process of claim 43, wherein the elastic material comprises a graphic registered in a machine direction relative to the first registration mark and the second registration mark.

55. The process of claim 54, wherein the graphic comprises the first registration mark.

* * * * *

UNITED STATES PATENT AND TRADEMARK OFFICE
CERTIFICATE OF CORRECTION

| | |
|---|---|
| PATENT NO. | : 7,047,852 B2 |
| APPLICATION NO. | : 10/001207 |
| DATED | : May 23, 2006 |
| INVENTOR(S) | : Kent Allan Franklin et al. |

It is certified that error appears in the above-identified patent and that said Letters Patent is hereby corrected as shown below:

In Column 6, line 19:
  Remove "18" and insert --19-- after "Equation".

Signed and Sealed this

Twenty-sixth Day of December, 2006

JON W. DUDAS
*Director of the United States Patent and Trademark Office*